United States Patent [19]
Vandenbergh et al.

[11] Patent Number: 5,965,414
[45] Date of Patent: *Oct. 12, 1999

[54] PROCESS FOR PRODUCING YEAST AND MOLD INHIBITING PRODUCTS WITH LACTOBACILLUS

[75] Inventors: Peter A. Vandenbergh, Sarasota, Fla.; Stephen W. King, Napa, Calif.

[73] Assignee: Microlife Technics, Inc., Sarasota, Fla.

[ * ] Notice: This patent is subject to a terminal disclaimer.

[21] Appl. No.: 07/905,132

[22] Filed: Jun. 23, 1992

Related U.S. Application Data

[63] Continuation of application No. 07/468,575, Jan. 23, 1990, abandoned, which is a continuation of application No. 07/082,118, Aug. 6, 1987, abandoned, which is a continuation-in-part of application No. 06/794,468, Nov. 4, 1985, Pat. No. 4,956,177.

[51] Int. Cl.$^6$ .................................................. C12P 1/04
[52] U.S. Cl. .................. 435/170; 435/252.9; 435/252.1; 424/93.45; 424/115
[58] Field of Search .................. 435/41, 252.1, 435/170, 252.9; 424/115, 93 J, 93.45

[56] References Cited

U.S. PATENT DOCUMENTS 3,689,640  9/1972  Shahani .................................... 424/118
4,956,177  9/1990  King ........................................... 424/93

FOREIGN PATENT DOCUMENTS 8001045  8/1980  Netherlands .
1109436  8/1984  U.S.S.R. .

OTHER PUBLICATIONS

ATCC catalogue of Bacteria, pp. 115–116, 1989.
Condensed Chemical Dictionary, p. 502, 1974.
The Merck Index, p. 768, 1983.
Vincent et al, *J. Bacteriol.*, vol. 78, pp. 477–484, 1959.
ATCC Catalogue of Bacteria, 1989, pp. 116–118.
Rehm et al, "Biotechnology", vol. 5, p. 73, 1983.

*Primary Examiner*—Irene Marx
*Attorney, Agent, or Firm*—Ian C. McLeod

[57] ABSTRACT

A method for producing a novel yeast and mold inhibiting products (FIC) from a Lactobacillus, particularly a *Lactobacillus casei* having the yeast and mold producing characteristics of *Lactobacillus casei* var. *rhamnosus* NRRL-B-15972 is described. The products (FIC) are particularly useful in retarding yeast and mold growth in foods and other materials in need thereof.

23 Claims, No Drawings

PROCESS FOR PRODUCING YEAST AND MOLD INHIBITING PRODUCTS WITH LACTOBACILLUS

CROSS REFERENCE TO RELATED APPLICATION

This is a continuation of application Ser. No. 07/468,575 filed on Jan. 23, 1990, now abandoned, which is a continuation of Ser. No. 07/082,118, filed Aug. 6, 1987, now abandoned, which is a continuation-in-part of Ser. No. 06/794,468, filed Nov. 4, 1985, now U.S. Pat. No. 4,956,177.

BACKGROUND OF THE INVENTION

1. Field of the Invention

The present invention relates to yeast and mold (fungus) inhibiting products produced by Lactobacillus species, particularly a *Lactobacillus casei* having the essential identification characteristics of *Lactobacillus casei* var. *rhamnosus* NRRL-B-15972. In particular, the present invention relates to a process for producing the products and to their use in preventing yeast and mold growth in foods and other materials.

2. Prior Art

Various substances are produced by microorganisms which are antimicrobial in character.

Lactobacillus are known to produce metabolic products that are antibacterial and allow them to compete more effectively in certain environments. It is not believed to be known that lactobacilli produce any separately isolatable metabolic products which inhibit yeast and mold.

OBJECTS

It is therefore an object of the present invention to provide novel Lactobacillus metabolic products which inhibit yeast and mold and which are referred to herein as "FIC" or fungal inhibiting compounds. Further it is an object of the present invention to provide a process for producing the FIC products as well as a method for using these FIC products in foods and other materials. These and other objects will become increasingly apparent by reference to the following description.

GENERAL DESCRIPTION

The present invention relates to a process for producing yeast and mold inhibiting products (FIC) which comprises: incubating live cells of a Lactobacillus species in a nutrient medium for the cells including a sulfur containing organic compound (preferably cysteine, garlic extract, whey, yeast, yeast extract, molasses or protein digest) which induces the formation of the products (FIC), a protein source, and a carbon source, so as to produce an isolatable amount of the products (FIC) in the nutrient medium, wherein the products (FIC) inhibit *Penicillium oxalicum* spores in an assay with the products (FIC) and the *Penicillium oxalicum* spores mixed.

The present invention relates to a process for producing yeast and mold inhibiting products (FIC) which comprises: incubating live cells of a Lactobacillus species in a nutrient medium containing growth factors present in cysteine, garlic extract, milk, whey, yeast, yeast extract, molasses or protein digest which induce the formation of the products (FIC), a protein source and a carbon source, so as to produce the products (FIC) in the nutrient medium; and treating the nutrient medium which has been incubated so as to produce the products (FIC) with or without the live cells, wherein the products (FIC) inhibit *Penicillium oxalicum* spores in an assay with the products (FIC) and the *Penicillium oxalicum* spores mixed.

Further still the present invention relates to a process for producing yeast and mold inhibiting products (FIC) which comprises: incubating live cells of a Lactobacillus having yeast and mold inhibiting characteristics of *Lactobacillus casei* var. *rhamnosus* NRRL-B-15972 in a nutrient medium for the cells containing growth factors present in cysteine, garlic extract, milk, whey, yeast, yeast extract, molasses or protein digest which induce the formation of the products (FIC), and a carbon source so as to produce products (FIC) in the nutrient medium wherein the products (FIC) inhibit *Penicillium oxalicum* spores in an assay with the products (FIC) and the *Penicillium oxalicum* spores mixed; and treating the nutrient medium which has been incubated so as to produce the products (FIC) with the cells disrupted.

Finally the present invention relates to a method for preventing yeast and mold growth in a material in need thereof which comprises: adding to the material products (FIC) produced by a process which comprises incubating live cells of a Lactobacillus in a nutrient medium containing a sulfur containing organic compound, a protein source and a carbon source which induce the formation of the yeast and mold inhibiting products (FIC) in the nutrient medium wherein the products (FIC) inhibit *Pencillium oxalicum* spores in an assay with the products (FIC) and the *Penicillium oxalicum* spores mixed and then treating the nutrient medium which now contains live cells, in such a manner so as to produce the final products (FIC) in a form containing live cells, dead cells or no cells to thereby prevent yeast and mold growth in the material.

The preferred products (FIC) from *Lactobacillus casei* var. *rhamnosus* NRRL-B-15972 have a molecular size of less than 1000 daltons and an ultraviolet absorbance at 269 nanometers. It is a complex mixture of compounds. U.S. application Ser. No. 794,468, now U.S. Pat. No. 4,956,177, described the use of *Lactobacillus casei* var. *rhamnosus* NRRL-B-15972 on various materials, particularly plants, to inhibit mold. It was thought when this application was filed that the live bacteria were necessary for mold inhibition.

*Lactobacillus casei* var. *rhamnosus* NRRL-B-15972 is described in application Ser. No. 794,468. It is deposited with the Northern Regional Research Laboratory in Peoria, Ill. U.S. application Ser. No. 794,468, now U.S. Pat. No. 4,956,177, described the use of *Lactobacillus casei* var. *rhamnosus* NRRL-B-15972. The characteristics of this strain are as follows:

(1) Characterization:

| Morphology - rods (typical of isolate): | | | |
|---|---|---|---|
| Gram rx | + | motility | − |
| Catalase | − | | |
| mannitol | + | | |
| mannose | + | | |
| melibiose | − | | |
| raffinose | − | | |
| galactose | ± | | |
| sorbitol | + | | |
| sucrose | + | | |
| adonitol | ± | | |
| arabinose | + | | |
| cellobiose | + | | |
| glucose | + | | |

-continued

| Morphology - rods (typical of isolate): | |
|---|---|
| dulcitol | − |
| salicin | + |
| glycerol | − |
| inositol | ± |
| lactose | + |
| maltose | + |
| xylose | − |
| trehalose | + |
| esculin | + |
| fructose | + |
| rhamnose | + |
| starch | − |
| nitrate reductase | − |
| ONPG | |

(2) Heavy growth in MRS broth (Difco, Detroit, Mich.) at a wide range of temperatures.

(3) Inhibits the following fungi on MRS agar and Potato Dextrose Agar supplemented with 1% Bacto-Peptone (PDAP)—(All media by Difco, Detroit, Mich.):

| | MRS | PDAP |
|---|---|---|
| P. oxalicum | + | ± |
| Geotricum candidum | − | − |
| Schlerotinia schlerotiorum | + | + |
| Botrytis cinereo | + | + |
| Verticillium sp. | + | − |
| Fusarium solani | + | + |
| Monilina fructicola | + | + |
| Aspergillus fumigatus | + | − |
| Aspergillus flavus | + | ± |
| Aspergillus terreus | + | ± |

(4) *L. casei* var. *Rhamnosus* NRRL-B-15972 grew in a defined medium (Folic Acid Assay Medium—Difco) and inhibited the above mentioned molds. Nutritional studies showed that yeast extract or molasses at 1% wt/v, added to the defined medium stimulated growth of NRRL-B-15972 and appeared to enhance the fungal inhibitory property of the bacteria.

Any Lactobacillus strain, whether naturally occurring or genetically engineered, with genetic material (in chromosomes or plasmids) encoding for similar yeast and mold inhibiting products (FIC) can be used to produce the products (FIC), although *Lactobacillus casei* var. *rhamnosus* NRRL-B-15972 appears to be the most effective naturally occurring (non-genetically engineered) source.

Various growth media for Lactobacillus can be used. The media must promote growth of cells and production of the products (FIC). Media to promote growth must contain protein and a carbon source. In addition, for products (FIC) production the media preferably includes a sulfur containing organic compound. Preferably the growth media include a sulfur containing organic compound, a protein source, a carbon source and minerals. Proteinaceous or amino acid materials from natural sources can include the sulfur containing compound. Thus protein sources such as milk, whey, yeast, yeast extract or protein digest can be a source of the sulfur compound and stimulate the production of the products (FIC). Separate compounds containing sulfur without being a protein source, such as garlic extract, molasses and cysteine, can be used. The carbon source can include fructose, sucrose, dextrose, lactose or molasses. Minerals which facilitate growth of the cells, such as manganese and magnesium salts are available in corn steep liquor or can be added as pure salts. Preferably buffers such as alkali metal phosphates are used to maintain the pH. It has been found that cinnamic acid and/or an alkali metal propionate and/or phenylalanine further stimulate the production of the yeast and mold inhibitory products (FIC) in the above referenced media. Preferably the cells are grown at a temperature between 10° and 50° C. Numerous variations of the nutrient medium and growth conditions will occur to those skilled in the art.

After growth of the cells, the nutrient medium preferably is processed to eliminate most of the live cells and then either concentrated or extracted to produce the yeast and mold inhibiting products (FIC). The yeast and mold inhibiting products (FIC) can be dried, lyophilized or frozen prior to use. The preferred process for producing the products (FIC) in a relatively unconcentrated form is spray drying the growth medium after the yeast and mold inhibitory products are produced in the medium. All of these methods are well known to those skilled in the art.

Various water immiscible solvents can be used to extract the products from the growth medium, such as lower alkyl alcohols and esters. Preferably n-butanol isopropanol, acetone, ethyl acetate or ethanol and combinations with water are used. The products can also be separated by chromatographic methods including molecular sieve, ion exchange and high pressure liquid chromatography methods well known to those skilled in the art. Impurities can be removed from the products (FIC) using molecular sieves and reverse osmosis. Essentially any chemical and/or mechanical process can be used for the separation.

As used herein, the term "material" means any surface in need of treatment by the FIC. The term material includes living and non-living surfaces. The yeast and mold inhibiting products (FIC) are preferably used in foods in an amount which inhibits *P. oxalicum* for at least 72 hours. The amount of FIC used depends upon the number of yeast and mold cells in the material to be treated.

Any food can be preserved by the method of the present invention especially carbonated beverages, Cottage cheese, yogurt, margarine, bread, grains and nuts. Because the products (FIC) are effective in a broad pH range pH 3 to 10 they are especially useful for use to preserve any food by the method of the present invention. The yeast and mold inhibiting products (FIC) are particularly useful in fermented foods and other preserved foods which are prone to such spoilage. Other food applications include silage and corn mold treatment and peanut treatment to prevent aflatoxin contamination by mold. Various materials can be treated and FIC can be used to prevent infection by mold and yeast, including living tissue as the material either in culture or in an animal, particularly mammals. Topical application of FIC to mammals either internal or external is preferred. Detergents, soaps and other cleansers can be combined with the products (FIC).

SPECIFIC DESCRIPTION

SUMMARY OF EXAMPLES

*Lactobacillus casei* var. *rhamnosus* NRRL-B-15972 produces products (FIC) which inhibit a wide variety of yeasts including: *P. camemberti, B. allii,* Caldosporium, Debaromyces sp., *S. cerevisiae* (Baker's) and molds. The compounds in the products (FIC) are polar and have a molecular size of less than 1,000 daltons and are not proteins, or lipids. The product (FIC) is unique in that it is insoluble in chloroform and n-hexane, and soluble in ethanol, n-butanol and acetone. The FIC appears to be temperature stable, i.e. −70° C. to +100° C., however it is destroyed by autoclaving at 121° C. FIC is stable from pH 3–10. Nutritional studies indicate that alkali metal propionate, phenylalanine, and/or cinnamic acid appear to further stimulate production of the yeast and mold inhibiting products by *Lactobacillus casei* var. *rhamnosus* as well as by other Lactobacilli. Purification of the products (FIC) can be obtained through the use of organic extraction and flash evaporation. The following examples show the method of production and use of the yeast and mold inhibiting products (FIC) of the present invention.

EXAMPLE 1

Lactobacillus sp. Exhibiting Antifungal Activity.

Antifungal products (FIC) are produced by Lactobacillus having various degrees of activity. These are shown in Table 1 wherein various cultures grown on agar were tested against *P. oxalicum* spores.

TABLE 1

|  | Fic Zone 48 h[1] |
| --- | --- |
| *Lactobacillus casei* var. *rhamnosus* NRRL-B-15972 | 5.0 mm |
| *L. casei* var. *casei* 2610 | 3.0 mm |
| *L. casei* var. *casei* 2661 | 4.0 mm |
| *L. casei* var. *tolerans* | 4.0 mm |
| *L. casei* VH | 4.0 mm |
| *L. plantarum* ATCC 8014 | 4.0 mm |
| *L. acidophilus* SFS[2] | No Zone Produced |
| *L. bulgaricus* YB-1[2] | 2.0 mm |
| *L. bulgaricus* DFW[2] | 3.0 mm |
| *L. bulgaricus* LBHW[2] | 3.0 mm |
| *L. bulgaricus* HCOYWC[2] | 3.0 mm |
| *L. parma* | No Zone Produced |

[1]The Cells were grown 24 h at 35° C. on MRS agar medium (DIFCO, Detroit, Michigan). MRS ™ contains yeast extract along with proteose peptone, beef extract, sodium acetate, sodium citrate and dextrose. Agar is added to form a gel. The live cells were then overlayed on the agar with $10^6$ spores/ml of the fungus *Penicillium oxalicum*. The width of the clear zone was measured.
[2]These cultures were grown in a confined chamber @ 35° C. with carbon dioxide and then challenged with the *P. oxalicum*. The *L. bulgaricus* and *L. casei* strains listed in Table 1 have different genetic and physiological characteristics. All of the strains are on deposit at Microlife Technics, Inc., Sarasota, Florida.

None of the Lactobacilli were as effective as *L. casei* var. *rhamnosus* NRRL-B-15972. This strain was used for the subsequent Examples.

EXAMPLE 2

Preparation, production and purification of liquid yeast and mold inhibiting products (FIC).

Medium Incubation—A culture of *Lactobacillus casei* var. *rhamnosus* NRRL-B-15972 was grown in MRS™ broth (Difco, Detroit, Mich.) supplemented with 1% by weight yeast extract (Oxoid®, Oxoid Ltd., Basingstoke, Hampshire, England). MRS™ contains yeast extract, proteose peptone, beef extract, sodium acetate, sodium citrate, and dextrose in a broth. One (1) liter of the medium was sterilized, inoculated with the culture and incubated at 35° C. without shaking or neutralization for 18 hours. The medium can be pasteurized or sterilized.

The purification procedure was:
1. Flash Evaporation—The cells and medium were concentrated (1 liter to 100 ml) using a flash evaporator (Roto-Vap™). A dark brown mixture remained (100 ml).
2. Butanol—The concentrated cells-medium suspension was then mixed with 1 liter of n-butanol. This mixture was placed in a separatory funnel and separation occurred in 30 minutes. The bottom water layer was discarded. The upper layer (n-butanol layer) was then concentrated using the flash evaporator until a dry particulate material remained. This material was then resuspended in 50 ml of distilled water.
3. Ethanol Extraction—To the 50 ml of distilled water mixture, 250 ml of ethanol (100%) was added and impurities were allowed to precipitate overnight at −70° C. After precipitation had occurred, the solution was centrifuged at −20° C. for 20 minutes at 12,000×g. The supernatant was then concentrated on the flash evaporator. The oily material was resuspended in 10 to 20 ml of distilled water.
4. Column Chromatography—A Pharmacia column (2.6 cm×35 cm) containing 125 g of silica gel (Sigma™, St. Louis Mo.). 28–200 mesh, 22 Angstrom mean pore diameter) was prepared. The silica gel was suspended in methanol, chloroform and ethyl acetate in a ratio of 1:2:3 respectively. The total column volume was 186 ml. Approximately 5 ml of the concentrated ethanol fraction was loaded onto this column. The column was washed with approximately 400 ml of the above solvent. The column washings were discarded.

The column was then washed with a mixture of water, 5% ammonium hydroxide, glacial acetic acid, acetone and n-butanol as in a ratio of respectively 2:3:3:5:7 as a solvent. The solvent was collected in 5 ml fractions. The 20th through 30th fractions which contained the antifungal substance were saved. These fractions were collected and concentrated using the flash evaporator and then resuspended in 5 ml of distilled water.
5. Acetone Precipitation—To 5 ml of the concentrated column material, 150 ml of acetone was added and precipitation was allowed to occur overnight at −70° C. to remove impurities. The supernatant was centrifuged, the acetone was flash evaporated on the flash evaporator and the resulting antifungal substance was resuspended in 3 ml of distilled water.

FIC was assayed using a) MRS (Difco) agar plates; b) MRS (Difco) soft agar, (1 g of Bacto™ (Difco) agar per 100 ml MRS broth) at 8 ml/plate tempered at 55° C.; c) *Penicillium oxalicum* spores $10^8$/ml in distilled water, at 1 ml per assay; and d) The material to be assayed.

Eight (8) ml of soft agar was combined with 1 ml of the spores ($10^8$/ml) and 1 ml of assay material, the mixture was vortexed and the contents were poured over an MRS plate and then incubated at 25° C. The plates then were examined for fungal growth. There is either growth or no growth on the plate. The degree of growth is rated between +1 and +4 as described hereinafter. The final purified product resulted in no growth of *P. oxalicum* after 96 hours.

EXAMPLE 3

This example shows an alternate extraction method for producing an FIC similar to Example 2.

Medium and Incubation—The culture was grown in Folic Acid Assay Medium (DIFCO, Detroit, Mich.) supplemented with 1% yeast extract (OXOID®) or 1% whey protein concentrate or 1% garlic extract. One liter of the medium was sterilized, inoculated with culture and incubated at 35° C. for 18 hours without shaking or neutralization.

The purification procedure was:
1. Butanol Extraction—The cells and medium suspension were mixed with 5 liters of n-butanol. The mixture was placed in a separatory funnel and the n-butanol layer was saved. This layer was then concentrated using the flash evaporator.
2. Ethanol Extraction—The above mixture (50 ml) was combined with 250 ml of ethanol (100%) and precipitated overnight at −70° C. The material was centrifuged at −20° C. for 20 minutes at 12,000×g. The supernatant was then decanted and concentrated using the flash evaporator.

3. Dialysis—The ethanol precipitate was then placed in a dialysis bag with 1000 dalton molecular size cut off. The bag and its contents were then dialyzed against distilled water (100 ml) at 4° C. for 18 h. The distilled water was then concentrated on the flash evaporator. FIC was assayed as in Example 2. The results are shown in Table 2.

TABLE 2*

| Growth Period | Folic Acid Assay Medium Unsupplemented | Folic Acid Assay Medium plus 1% yeast extract | Folic Acid Assay Medium Plus 1% Whey Protein Concentrate | Folid Acid Assay Medium Plus 1% Garlic Extract |
|---|---|---|---|---|
| 24 h | +1 | — | — | — |
| 48 h | +2 | +1 | — | — |
| 96 h | +4 | +2 | +1 | — |

*assayed as in Example 2 with a spore concentration of $10^7$ spores per ml.
— = no mycelial masses present.
+1 = mycellial masses present, greater than 1000.
+2 = confluent white lawn.
Folic acid based assay medium supplemented with 1% garlic extract produced the highest concentration of FIC.

EXAMPLE 4

Comparison of the Expression of FIC by *L. casei* var. *rhamnosus* NRRL-B-15972 In Various Nutrient Media.

*Lactobacillus casei* var. *rhamnosus* NRRL-B-15972 was inoculated into 250 ml of various nutrient media and incubated at 35° C. for 18 hours. The cells and media were then extracted and processed as previously described in Example 2. One ml of extracted material was then assayed using the fungal biological method of Example 2, and with a spore concentration of $10^7$ spores per ml. The assay plates were examined for fungal growth after 24 hours, 48 hours and 72 hours incubation, respectively. The results are shown in Table 3.

TABLE 3

| Medium | Incubation Time | | |
|---|---|---|---|
| | 24 h | 48 h | 72 h |
| Control uninoculated MRS broth (Difco ®) supplemented with 1% yeast extract (Oxoid ®). | +1 | +4 | +4 * |
| MRS Broth (Difco ®). | — | +2 | +4 |
| Whey based broth supplemented with 1% yeast extract (Oxoid ®). | +1 | +4 | +4 |
| MRS broth (Difco ®) supplemented with 1% yeast extract (Oxoid ®) | — | — | +1 |
| MRS broth (Difco ®) supplemented with 1% yeast extract (Tureen ®) | — | +1 | +2 |
| MRS broth (Difco ®) supplemented with 0.01% sodium propionate | — | — | — |
| MRS broth (Difco ®) supplemented with 0.01% cinnamic acid | — | — | — |
| MRS broth (Difco ®) supplemented with 0.01% phenylalanine | — | — | — |
| Corn steep based medium including 4% Corn steep, 5% lactose, 0.01% sodium propionate, 0.2% sodium citrate, 1.0% Edamin (enzymatic digest of lactalbumin) S (Kraft, Sheffield Products, Kraft, Inc., Norwich, N.Y.) | | | |

*— = No mycelial masses present.
+1 = Mycelial masses present greater than 1000.
+2 = Confluent white lawn.
+3 = Confluent lawn piled in mass.
+4 = Confluent lawn pigments green.

The above results indicate that the selection of the nutrient medium is important for production of the products (FIC). Even when a whey based medium was supplemented with yeast extract to obtain good Lactobacillus cell growth, sufficient products (FIC) were not produced. Also, the above results indicate that not only are the medium ingredients important for the products (FIC) production, but the brand of a particular ingredient also is important. If Oxoid® yeast extract in the medium was substituted with another brand of yeast extract, Tureen®, expression of the products (FIC) was reduced. The MRS Difco® medium supplemented with 1% Oxoid® yeast extract produced the highest level of the products (FIC) production and thus the best fungal inhibition. Cinnamic acid, phenylalanine and sodium propionate all enhanced production of FIC.

EXAMPLE 5

Preparation and Production of Dried FIC For Food Application. *Lactobacillus casei* var. *rhamnosus* NRRL-B-15972 was grown in broth consisting of the following components: 2% lactose, 1% nonfat dry milk, 1% yeast extract, 0.36% $Na_2HPO_4$, 0.56% $KH_2PO_4$ and trace amounts of $MgSO_4$ and $MnSO_4$. The inorganic salts $Na_2HPO_4$ and $KH_2PO_4$ were made ten (10) times more concentrated than necessary and then added to the growth medium after autoclaving. One (1) liter of the medium was sterilized at 121° C. for 15 minutes inoculated with the culture and incubated at 35° C. without shaking for 18 hours.

After the culture was grown 18 hours at 35° C. in the above medium, the culture flask was then placed in a 70° C. incubator for 45 minutes, to heat inactivate the culture. The nutrient medium was then lyophilized 18 hours. From 25 ml of liquid nutrient medium, 1.2 g of dried products (FIC) was obtained.

The titration of the dried products (FIC) with a constant fungal concentration of $10^7$ *P. oxalicum* spores per ml, as in Example 2, is shown in Table 4.

TABLE 4

| Growth Period | Amount of dried products (FIC) (g/ml) | | | | | Control |
|---|---|---|---|---|---|---|
| | 0.3 | 0.4 | 0.6 | 1.2 | 2.4 | 0.0 |
| 24 h | — | — | — | — | — | + |
| 48 h | +3 | +3 | +3 | +1 | — | +3 |
| 72 h | +4 | +4 | +4 | +3 | — | +4 |

— = means no mycelial masses present
+1 = visible mycellial masses
+2 = whitelawn of mycellial masses
+3 = white dented lawn of mycelium
+4 = final green pigmentation of mycelium Titration of 1 g of the dried products (FIC) with a variable number of fungal spores at 25° C. is shown in Table 5.

TABLE 5

| Growth Period | Number (of spores per ml) $10^7$ | $10^6$ | $10^5$ | $10^4$ | Media Control | FIC Control | Fungus Control[a] |
|---|---|---|---|---|---|---|---|
| 24 h | — | — | — | — | — | — | +1 |
| 48 h | +2 | +2 | +1 | — | — | — | +2 |
| 72 h | +4 | +4 | +4 | +1 | — | — | +4 |

+1 = visible mycelial masses
+2 = white lawn of mycellial masses
+3 = white dented lawn of mycelium
+4 = final green pigmentation of mycelium
[a] $10^7$ spores per ml The above results indicate that a dried non-extracted FIC preparation exhibits fungal inhibition.

EXAMPLE 6

Use of Dried Products (FIC) to Extend the Shelf Life of Cottage cheese.

The products (FIC) of Example 5 was sprayed onto surface of Cottage cheese and $10^5$ P. oxalicum spores per ml were added to the Cottage cheese. The products (FIC) were used in a concentration of 1.0 gram per ml. About 35 grams of Cottage cheese were used per test. The tests were conducted at 25° C. The results are shown in Table 6.

TABLE 6

| Growth Period | Cottage chesse without FIC and added fungus | Cottage cheese with added fungus only | Cottage cheese with FIC only | Cottage cheese with added fungus and Dried FIC |
|---|---|---|---|---|
| 24 h | — | — | — | — |
| 48 h | — | — | — | — |
| 72 h | — | — | — | — |
| 96 h | — | +4 | — | — |

— = no mycelial masses present.
+4 = final green pigmentation of mycelium, not edible,.

The products (FIC) of the present invention will inhibit up to $10^7$ spores per ml of *Penicillium oxalicum* for at least 24 hours in the least concentrated form. The products (FIC) will easily inhibit up to $10^3$ spores per ml which is a very significant mold population in a material. A mold population of greater than 10 per ml is significant.

It is intended that the foregoing description be only illustrative of the present invention and that the present invention be limited only by the hereinafter appended claims.

We claim:

1. A process for producing yeast and mold growth inhibiting products (FIC) which comprises:
   (a) incubating live cells of Lactobacillus having all of the identifying characteristics of *Lactobacillus casei* var. *rhamnosus* NRRL-B-15972 in a nutrient medium for the cells containing effective amounts of a sulfur containing organic compound which induce the formation of the products (FIC) and of a carbon source so as to produce an isolatable amount of the products (FIC) in the nutrient medium; and
   (b) recovering the products (FIC) from the nutrient medium, wherein the products (FIC) are polar, non-protein, non-lipid, have a molecular size of less than 1000 daltons, insoluble in chloroform or hexane and soluble in ethanol, in butanol and acetone, are temperature stable at between −70° C. and 100° C. and are stable at a pH between 3 to 10.

2. A process for producing yeast and mold growth inhibiting products (FIC) which comprises:
   (a) incubating live cells of a Lactobacillus having all of the identifying characteristics of *Lactobacillus casei* var. *rhamnosus* NRRL-B-15972 in a nutrient medium for the cells containing effective amounts of growth factors present in a composition selected from the group consisting of cysteine, garlic extract, milk, whey, yeast, a yeast extract, molasses and a protein digest which induce the formation of the products (FIC), of a protein source and of a carbon source, so as to produce the products (FIC) in the nutrient medium; and
   (b) treating the growth medium which has been incubated so as to recover isolatable amounts of the products (FIC); and
   (c) recovering the products FIC from the nutrient medium, wherein the products (FIC) are polar, non-protein, non-lipid, have a molecular size of less than 1000 daltons, are insoluble in chloroform or hexane and soluble in ethanol, in butanol and acetone, are temperature stable at between −70° C. and 100° C. and are stable at a pH between 3 to 10.

3. The process of claim 2 wherein the nutrient medium which is incubated contains the yeast extract for the growth factors, non-fat dry milk as the protein source; lactose, sucrose, dextrose, fructose or molasses as the carbon source and corn steep liquor as a source of minerals.

4. The process of claim 3 wherein the nutrient medium contains a compound selected from the group consisting of cinnamic acid, an alkali metal propionate and phenylalanine, in an amount which increases the production of the products (FIC).

5. The process of claim 2 wherein in step (b) the growth medium with the live cells is dried.

6. A process for producing yeast and mold growth inhibiting products (FIC) which comprises:
   (a) incubating live cells of a Lactobacillus having all of the identifying characteristics of *Lactobacillus casei* var. *rhamnosus* NRRL-B-15972 in a nutrient medium for the cells containing effective amounts of growth factors present in a composition selected from the group consisting of cysteine, garlic extract, milk, whey, yeast, a yeast extract, molasses and a protein digest which induce the formation of the products (FIC), a protein source and of a carbon source to thereby produce isolatable amounts of products (FIC) in the nutrient medium; and
   (b) treating the nutrient medium which has been incubated to recover the products (FIC) with removal of water from the nutrient medium to produce the products (FIC), wherein the products (FIC) are polar, non-protein, non-lipid, have a molecular size of less than 1000 daltons, are insoluble in chloroform or hexane and soluble in ethanol, in butanol and acetone, are temperature stable at between −70° C. and 100° C. and are stable at a pH between 3 to 10.

7. The process of claim 6 wherein in step (b) the nutrient medium is lyophilized.

8. The process of claim 6 wherein the Lactobacillus are incubated in the nutrient medium at a temperature of between about 100 and 50° C.

9. The process of claim 6 wherein the nutrient medium contains the yeast extract, whey or non-fat dry milk as the protein source, lactose, sucrose, dextrose, fructose or molasses as the carbon source and corn steep liquor as a source of minerals.

10. The process of claim 9 wherein the nutrient medium contains in addition a manganese salt, a magnesium salt and an alkali metal phosphate.

11. A process for producing yeast and mold growth inhibiting products (FIC) which comprises:
(a) incubating cells of a Lactobacillus having all of the identifying characteristics of *Lactobacillus casei* var. *rhamnosus* NRRL-B-15972 in a nutrient medium for the cells containing effective amounts of growth factors present in compositions selected from the group consisting of cysteine, garlic extract, milk, whey, yeast, a yeast extract, molasses and a protein digest which induce the formation of the products (FIC) and of a carbon source so as to produce the products (FIC) in the nutrient medium;
(b) mixing the incubated nutrient medium with an organic solvent which extracts the products (FIC) into the solvent;
(c) separating the solvent with the extracted products (FIC) from the nutrient medium; and
(d) separating the products (FIC) from the solvent, wherein the products (FIC) are polar, non-protein, non-lipid, have a molecular size of less than 1000 daltons, are insoluble in chloroform or hexane and soluble in ethanol, in butanol and acetone, are temperature stable at between −70° C. and 100° C. and are stable at a pH between 3 to 10.

12. The process of claim 11 wherein the solvent is n-butanol.

13. The process of claim 11 wherein the solvent is acetone.

14. The process of claim 11 wherein the solvent is ethanol.

15. The process of claim 11 wherein the solvent mixture is cooled to thereby precipitate impurities.

16. The process of claim 11 wherein in addition the separated products are purified to separate impurities using liquid chromatography.

17. The process of claim 11 wherein in addition the products (FIC) are purified by liquid dialysis which passes compounds through a membrane having a molecular size of about 1000 or less and wherein the products pass through the membrane and are collected.

18. The process of claim 17 wherein in addition the purified products (FIC) are further purified by liquid chromatography using a solvent mixture to produce separation of the products (FIC) from impurities.

19. The process of claim 18 wherein in addition the products (FIC) with out the impurities are subjected to a further purification using liquid chromatography.

20. The process of claim 11 wherein the nutrient medium contains the yeast extract and the protein digest.

21. The process of claim 1 wherein the nutrient medium which is to be incubated is pasteurized or sterilized prior to incubating the cells.

22. A process for producing fungal growth inhibiting products (FIC) which comprises:
(a) incubating cells of a Lactobacillus having all of the identifying characteristics of *Lactobacillus casei* var. *rhamnosus* NRRL-B-15972 in a nutrient medium for the cells containing effective amounts of growth factors present in cysteine, garlic extract, milk, whey, yeast, yeast extract, molasses or protein digest which induce the formation of the products (FIC), of a protein source and of a carbon source so as to produce the products (FIC) in the nutrient medium; and
(b) recovering the products (FIC) from the nutrient medium and cells, wherein the products (FIC) are polar, non-protein, non-lipid, have a molecular size of less than 1000 daltons, are insoluble in chloroform or hexane and soluble in ethanol, in butanol and acetone, are temperature stable at between −70° C. and 100° C. and are stable at a pH between 3 to 10.

23. A process for producing fungal growth inhibiting products (FIC) which comprises:
(a) incubating live cells of a Lactobacillus having all of the identifying characteristics of *Lactobacillus casei* var. *rhamnosus* NRRL-B-15972 in a nutrient medium containing effective amounts of growth factors for the cells which stimulate the cells to produce an isolatable amount of the products (FIC) in the nutrient medium; and
(b) recovering the products (FIC) from the nutrient medium, wherein the products (FIC) are polar, non-protein, non-lipid, have a molecular size of less than 1000 daltons, are insoluble in chloroform or hexane and soluble in ethanol, in butanol and acetone, are temperature stable at between −70° C. and 100° C. and are stable at a pH between 3 to 10.

* * * * *

UNITED STATES PATENT AND TRADEMARK OFFICE
CERTIFICATE OF CORRECTION

PATENT NO. : 5,965,414
DATED : October 12, 1999
INVENTOR(S) : Peter A. Vandenbergh and Stephen W. King It is certified that error appears in the above-identified patent and that said Letters Patent is hereby corrected as shown below:

Column 5, line 23, Table 1, "*L. casei* var. *casei* 2661" should be --*L. casei* var. *casei* 2601--.

Column 10, line 62 (Claim 8), "about 100 and 50°C" should be --about 10 and 50°C--.

Signed and Sealed this

Eleventh Day of April, 2000

Attest:

Q. TODD DICKINSON

Attesting Officer

Director of Patents and Trademarks